United States Patent [19]

Mansfield et al.

[11] Patent Number: 4,519,704
[45] Date of Patent: May 28, 1985

[54] MEASUREMENT OF OPTICAL REFRACTIVE INDEX PROFILES

[75] Inventors: Robert J. Mansfield, Wallingford, Conn.; David N. Payne, Southampton, England; Issei Sasaki, Sapporo, Japan

[73] Assignee: National Research Development Corporation, London, England

[21] Appl. No.: 476,465

[22] Filed: Mar. 18, 1983

[30] Foreign Application Priority Data

Mar. 18, 1982 [GB] United Kingdom ............... 8207968

[51] Int. Cl.³ ............................................. G01N 21/41
[52] U.S. Cl. .................................... 356/73.1; 356/128
[58] Field of Search ........................ 356/73.1, 128, 133

[56] References Cited

U.S. PATENT DOCUMENTS 4,349,276  9/1982  Vita ..................................... 356/73.1
4,361,402  11/1982 Costa .................................... 356/73.1
4,441,811  4/1984  Melezoglu et al. ............ 356/73.1 X

OTHER PUBLICATIONS

Brinkmeyer, "Refractive-Index Profile Determination of Optical Fibers by Spatial Filtering", Applied Optics, 1-1978, pp. 14-15.

Primary Examiner—Vincent P. McGraw
Assistant Examiner—S. A. Turner
Attorney, Agent, or Firm—Cushman, Darby & Cushman

[57] ABSTRACT

To determine the radial profile of the refractive index of a substantially cylindrical transparent object such as an optical fibre or optical fibre preform, the object is illuminated with a collimated beam of light incident at an angle to the axis of the cylindrical object differing substantially from 90 degrees and measuring the refraction angle at which light leaves a substantially plane endface as a function of the radial position on the endface.

13 Claims, 20 Drawing Figures

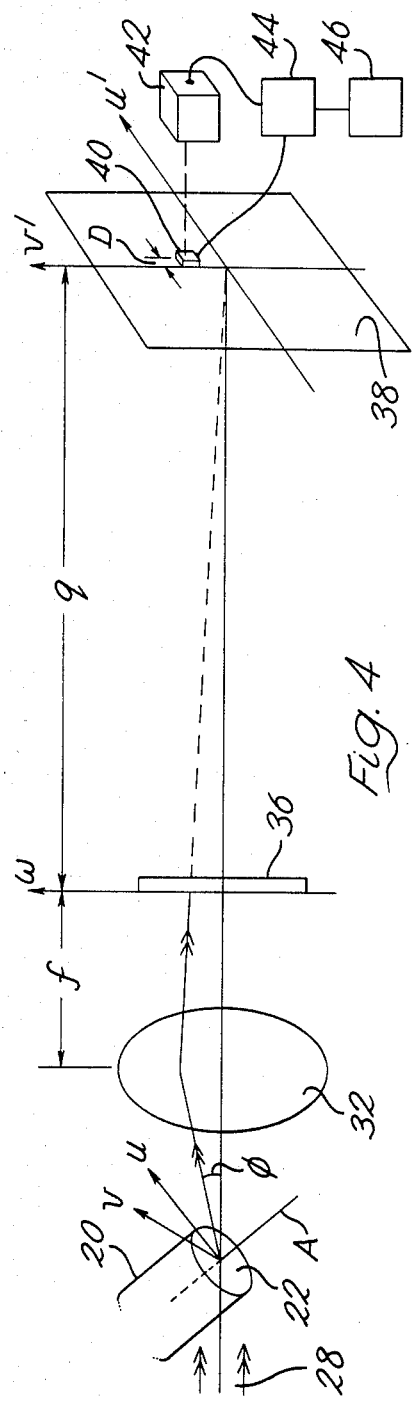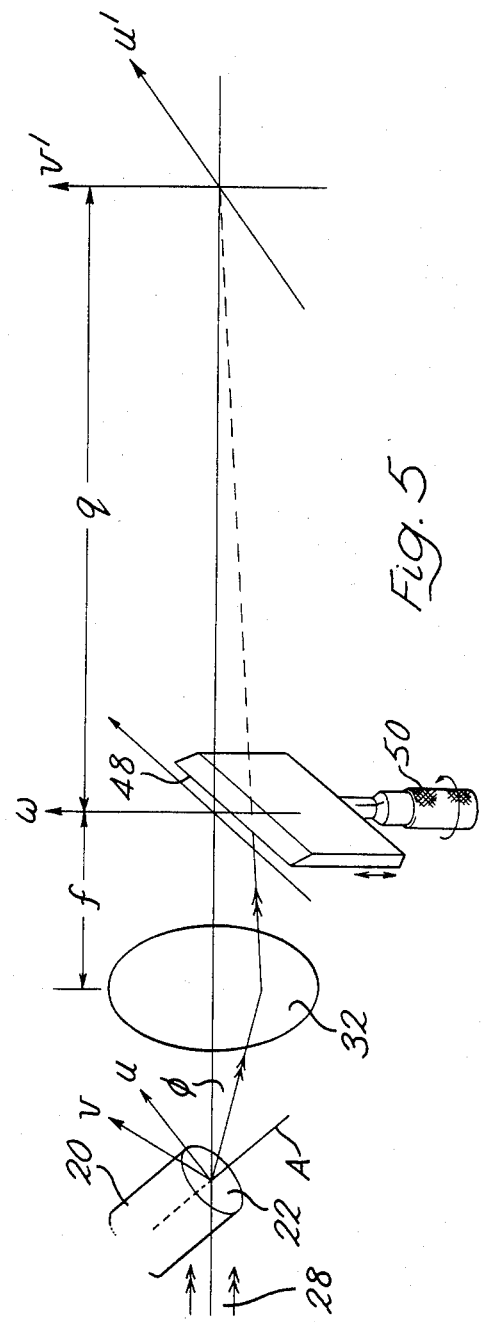
Fig. 4
Fig. 5

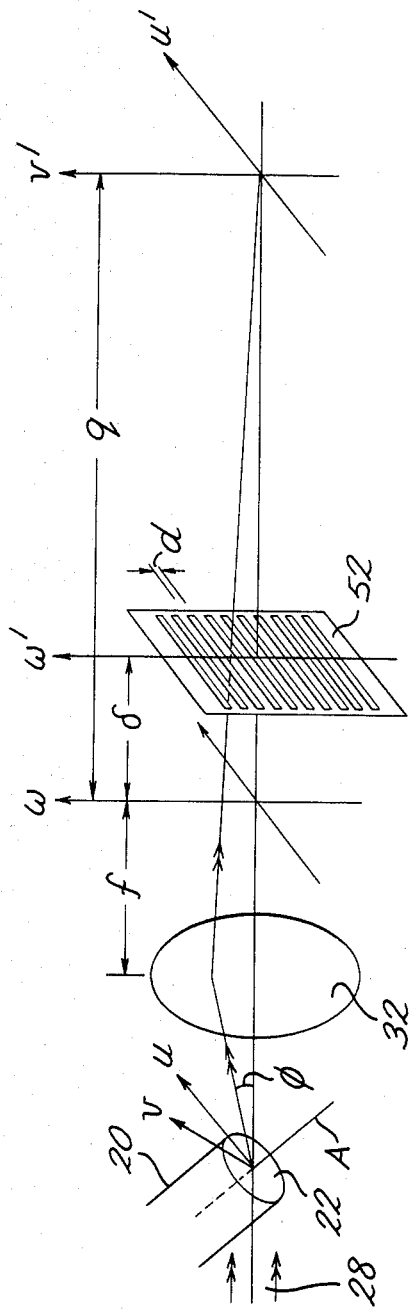
Fig. 8
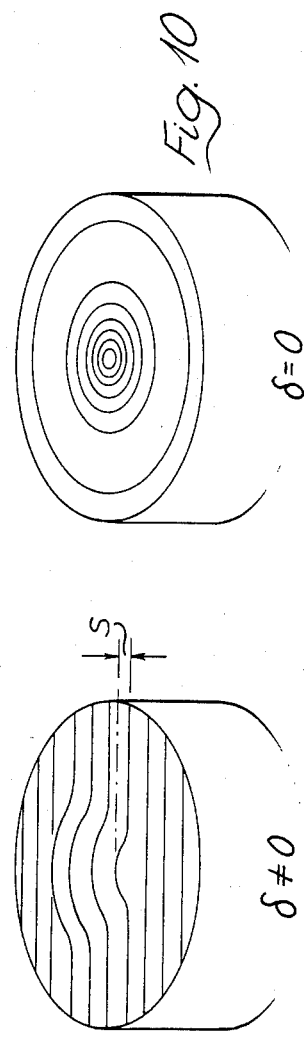
Fig. 9
Fig. 10

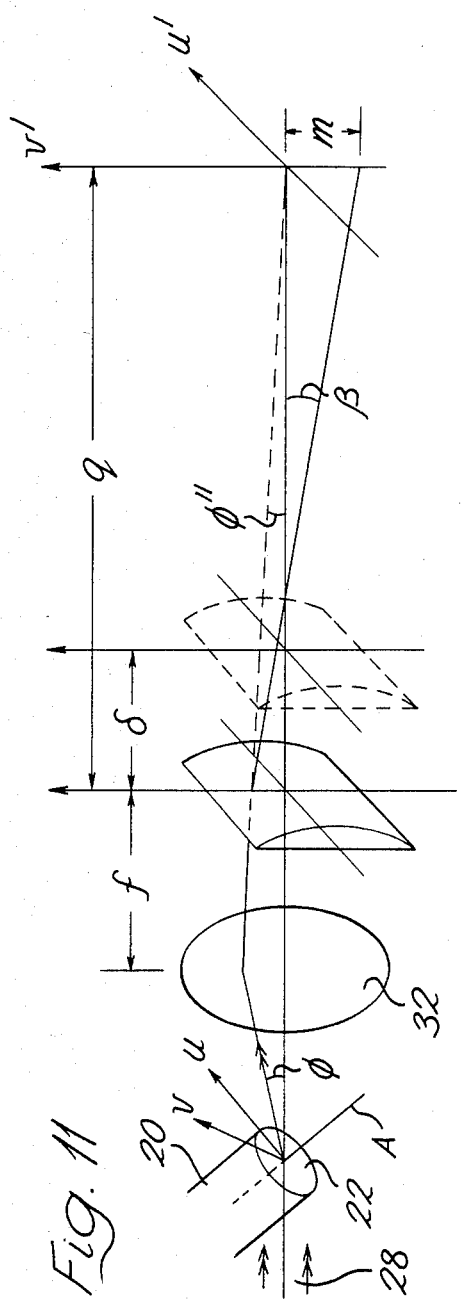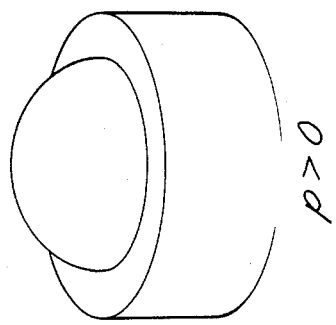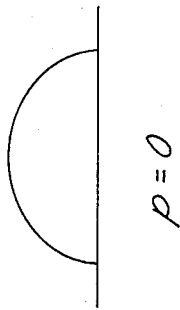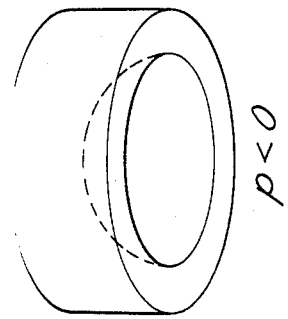
Fig. 11
Fig. 12a  p<0
Fig. 12b  p=0
Fig. 12c  p>0

MEASUREMENT OF OPTICAL REFRACTIVE INDEX PROFILES

This invention relates to the measurment of radial refractive index profile in an approximately cylindrical object which is essentially invariant (or slowly varying) along its length.

The specification of our co-pending UK patent application No. 81 07603 describes the measurement of the optical deflection function and/or the radial refractive index profile of an essentially cylindrical object such as an optical fibre or an optical fibre preform.

The cylindrical object is illuminated by a collimated beam perpendicular to the cylindrical axis. Light transmitted through the curved sides is refracted by the radial variation in refractive index, is then focussed and modulated so that the deflection function can be derived, and from that function the refractive index profile can be obtained by a mathematical transformation.

The present invention relates to a further method of sensing the refractive index profile, usually of an optical fibre preform, but possibly also of a single optical fibre, in which the profile is obtainable without use of a mathematical transformation.

According to the invention there is provided a method of measuring radial variations in the refractive index of an approximately cylindrical, translucent object having a substantially plane end face and a substantially invariant refractive index in a direction parallel to its axis, comprising illuminating the end face by means of a collimated beam of light incident at an angle to the cylindrical axis which differs substantially from 90 degrees and measuring at a plurality of radial positions the refractive angle at which light leaves the end face.

There is also provided apparatus for measuring radial variations of refractive index as claimed in claim 5 having modulating means positioned in the path of said light beam between said focussing means and said sensing means.

Usually the endface will be perpendicular to the cylindrical axis, and usually the light will pass first through the curved surface and then to the endface so that the angle of exit of light from the object is measured, but it is also possible for the light to be directly incident on the endface, with measurement of the angle at which light passes from the endface into the object. The measurement is practicable when the illuminating beam makes an angle of up to 60° with the plane of the endface; at greater angles the length of travel in the preform is so great that accuracy is lost. Usually the light will pass into and out of the object through an index-matching liquid which has an index approximately equal to that of the cylinder outer surface.

The refraction angle at which light leaves the endface may be measured as a function of position on the endface by probing the object with a thin pencil of light, such as from a laser, and directly measuring the beam deflection. Alternatively, the measurement can be made by illuminating all or part of the endface with a broad light beam, focussing said light with a lens so that in the focal plane of said lens the distance of transmitted light from the optical axis in a direction coplanar with the endface of the object is approximately linearly proportional to the angle through which light has been deviated by the object; optically modulating the focused light so that a property of the light varies as a function of said distance; and receiving the modulated light in an image plane, whereby the refractive index profile of the preform can be derived.

The optical modulation may be such that either a spatial or a temporal property of the light varies in the required direction.

In the accompanying drawings,

FIG. 1 illustrates the optical path through a cylindrical object during measurement according to the prior art method described in UK patent application No. 81 07603. The invention will be described with reference to the other FIGS. in which:

FIG. 4 illustrates modulation by a neutral density filter;

FIGS. 5 and 6 illustrate modulation by a knife edge in two different axial positions and FIG. 7 illustrates a shadowgraph image;

FIG. 8 illustrates use of a grating plate or a multicolour grating plate and FIGS. 9 and 10 show two possible images;

FIG. 11 illustrates use of a cylindrical lens, and FIGS. 12($a$), ($b$) and ($c$) show three possible images;

Figure 1:
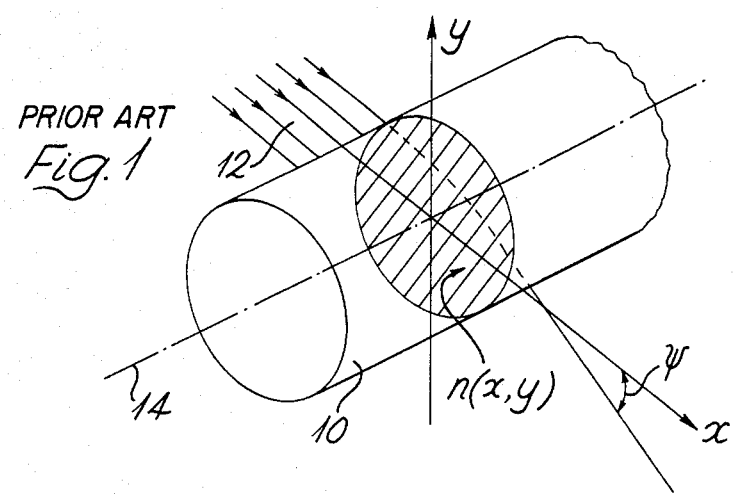

In the prior art arrangement of FIG. 1, an object 10 such as an optical fibre or an optical fibre preform is illuminated over part or the whole of its diameter by a collimated beam of light 12 incident at right angles to the cylindrical axis 14 of the object. The passage of a single light ray throught the object is shown, and the change of direction through angle is related to the refractive index profile in the shaded plane (x,y) perpendicular to the axis. It can be seen that light enters and leaves through the curved walls of the object. Various optical arrangements can be used to determine the profile and are described in UK patent application No. 81 07603; some arrangements can be applied to the present invention.

Figure 2:
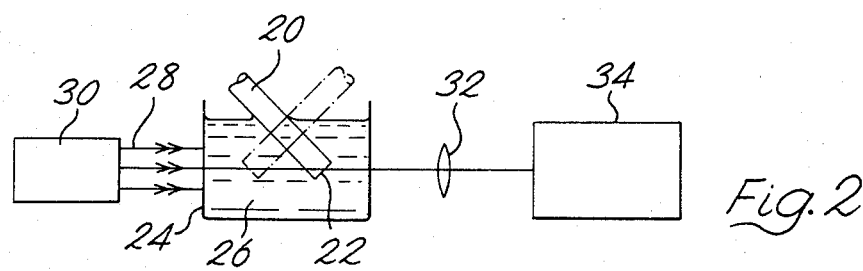
FIG. 2 illustrates schematically the general optical arrangement according to the invention.

The general arrangement according to the present invention is shown in FIG. 2 in highly schematic form. A generally cylindrical optical fibre preform 20 has a flat endface 22 perpendicular, or at a known angle, to the cylindrical axis of the preform. The preform is immersed in a bath 24 of index-matching liquid 26 and a beam of collimated light 28 (indicated by is central ray) from a source 30 is incident on the preform adjacent the endwall at an angle of 45° to the preform cylindrical axis, light entering the preform through its curved surface, and exiting through the endface 22. Transmitted light passes through a spherical lens 32 to a sensing system 34, which senses, as a function of position on the endface 22, the angle at which light leaves the preform 20. The sensing system can take many forms which will be described below.

An alternative position of the preform 20 is shown dotted; light then enters the endface and leaves through the curved walls, and measurement of angle is made through the curved walls.

Figure 3:
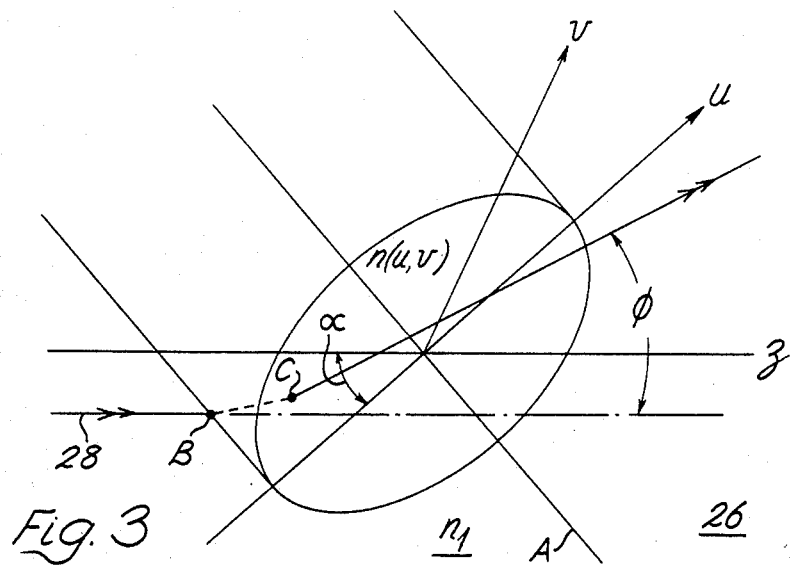
FIG. 3 shows the endface and an input and output ray of light.

FIG. 3 shows the endface 22 and adjacent curved walls of the preform 20; the preform cylindrical axis is indicated at A. The refractive index of the index-matching fluid 26 is $n_1$, and the refractive index $n(u,v)$ of the preform 20 varies over the endface 22 as a function of position, $(u,v)$, where the axes u and v in the plane of the endface 22 are shown.

The illuminated beam is incident on the preform 20 at an angle $\alpha$ to the plane of the endface 22. The passage of one light ray indicated by the double arrow, is shown; the ray is incident on the curved wall at point B, passes through the preform as indicated by the dotted line, and exits from the preform through the endface 22 at point C. The ray has been deviated from its original direction, shown chain-dotted, by an angle $\phi$.

We have discovered that this refraction angle $\phi$ is related and is nearly proportional to the refractive index of the preform at the point on the endface at which the ray leaves the preform. Our inventive method and apparatus are based on this discovery. Thus measurement of angle $\phi$ as a function of position on the endface gives measure of the refractive index profile of the preform without the need for numerical transformation. Not only can measurement be made directly, but the index profile of a non-circular preform can be determined easily; considered now theoretically it can be shown that:

$$\cos^2(\alpha - \phi) = \frac{n^2(u,v)}{n_1^2} - \sin^2\alpha \quad (1)$$

When, as is usually the case, the preform is immersed in an index-matching liquid, the ray at refraction angle $\phi$ experiences a further refraction on emerging into air, given by $\phi_a = n_1\phi$, which must be taken into consideration. Here $\phi_a$ is the refraction angle in air. Equation (1) holds, provided it is taken that $$\cos\phi \; \underline{\Omega} \; 1, \; \sin\phi \; \underline{\Omega} \; \phi \quad (2)$$

and $$2\Delta(u,v) = \frac{n^2(u,v) - n_1^2}{n_1^2} \; \underline{\Omega} \; \frac{\Delta 2 \; n(u,v)}{n_1} \quad (3)$$

If the relative index differences $\Delta$ between different parts of the endface are small, then there is a simple relationship:

$$\Delta(u,v) \; \underline{\Omega} \; \frac{\phi_a \sin|2\alpha|}{2n_1} \quad (4)$$

A plot of $n(u,v)$ as a function of angle $\phi$ for various values of angle $\alpha$ (not illustrated) shows that for $\Delta n(u,v)$ up to 0.02, the approximation of Equation (4) is valid, so that the measurement of refraction angle is linearly related to the refractive index at the exit point on the endface.

It is believed that it has not previously been realised that this simple relationship exists. Thus a method and apparatus according to the invention rely on the measurement of angle as a function of position to determine the refractive index profile.

Preferably by provision of the spherical lens 32 (FIG. 2) the angular deviation in air $\phi_a$ of a ray is converted in the focal plane of the lens to a linear position along an axis w in that plane, where the axis lies in the plane containing the preform axis A. The usual lens transfer equation applies, i.e.

$$w = f \tan\phi_a \quad (5)$$

where f is the focal length of the lens. The relationship is illustrated in FIG. 4.

From Equation (5) it can be seen that when $\phi_a$ is small, w is almost linearly related to $\phi_a$, and therefore to the refractive index of the corresponding point on the endface 22. Therefore by modulation of the light passing through the lens 32, the light distribution in the focal plane of the lens, and hence the local refraction angle, can be determined. The modulation can be spatial or temporal, and can either produce a direct display of a pattern related to index profile, or can produce measurable data which can be converted into a graphic display.

Some of the many forms of the sensing system 34 by which the refraction angle $\phi$ as a function of endface position $(u,v)$ can be measured will now be described, by the following examples are by no means exhaustive.

FIG. 4 illustrates a first method of applying spatial modulation. In the focal plane of the lens 32 is neutral density filter 36 having a linear (or other known) attenuation in the w direction. The intensity in the image in an image plane 38 is therefore related to the local refractive index in the endface 22.

Let $T_o$ be the trnsmission of the filter 36 at $w = 0$, and T be the transmission elsewhere, then if a is a constant, we can define the transmission T of the filter as:

$$T = aw + T_o \text{ where } 1 \geq T \geq 0 \quad (6)$$

The intensity I of the modulation image in the image plane $u', v'$ at a distance q from the filter 36 is then:

$$I(u',v') = I_o\left( \frac{2af\Delta n(u,v)}{\sin|2\alpha|} + T_o \right) \quad (7)$$

where $I_o$ is the uniform intensity of the image in the absence of the filter. The endface co-ordinates u,v are related to the image co-ordinates $u', v'$ by the usual lens formulae:

$$u' = \frac{-q \, u \sin\alpha}{f} \quad (8)$$

$$v' = \frac{-q \, v}{f} \quad (9)$$

Thus the density-graded image in the plane $u', v'$, gives a picture of the refractive index distribution on the endface 22. To measure the index profile, a small photodiode 40 of diameter D is scanned across the image plane 38 by a stepping device 42 controlled by a control unit 44. Alternatively, the preform can be translated and the photodiode kept stationary. The intensity sensed by the photodiode 40 is supplied to the control unit which supplies to a visual display unit 46 a two dimensional display of the refractive index profile in the endface 22.

FIG. 5 illustrates the use of a straight knife edge 48 arranged in the focal plane of the lens 32 and parallel to the u and u' axes. The knife edge can be stepped across the focal plane in the w direction by a micromanipulator 50. The movement progressively removes light rays in accordance with their angle of refraction $\phi$. At any position $w_c$ of the knife edge all areas of the image in the image plane $(u',v')$ with $< w_c$, i.e. with $n < n_c$, will be dark due to the knife edge shadow, where $n_c$ is the index at the shadow edge in the preform endface image, and from Equation (4) is given by:

$$N_c = n_1 + \frac{w_c}{2f} \sin|2\alpha| \quad (10)$$

Thus a reading of $w_c$ from the micromanipulator dial allows the determination of the index at the shadow boundary. The image will in general be an illuminated oval centre with a dark annular outer ring indicating the extinguished rays. As the knife edge approaches the optical axis of the apparatus it progressively removes the more highly deflected rays and the areas of low index are gradually extinguished. Thus the dark area increases, and when the knife edge is on the axis all light from the background index-matching fluid is intercepted, leaving illuminated only those areas of the preform with index higher than the fluid. Measurement of the corresponding knife edge position $w_c$ and the position of the dark area boundary relates refractive index to position in the endface. An automatic measurement can be made using a photodiode (not shown) scanned across the image plane.

Figure 6:
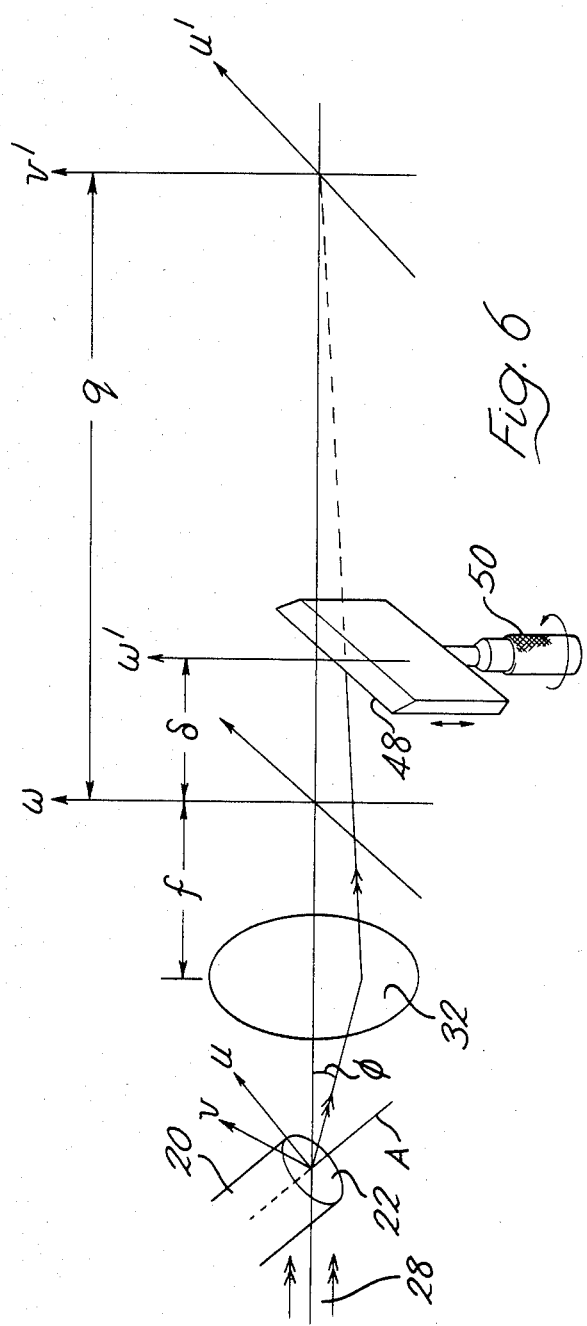
Figure 7:
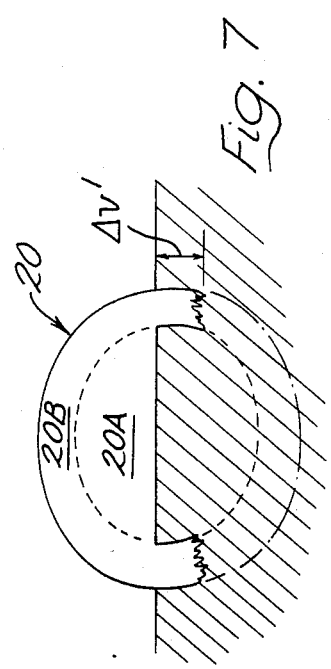

FIG. 6 illustrates a modification of FIG. 5 in which the knife edge 48 is positioned out of the focal plane at a distance $(f+\delta)$ from the lends 32; a slightly different shadow pattern is observable in the image plane u',v'; the shadow boundary co-ordinate y' is given by:

$$v' = \frac{w'q}{\delta} + w\left(1 - \frac{q}{\delta}\right) = \frac{w'q}{\delta} + \Delta v' \quad (11)$$

where w' is the distance of the knife edge from the optic axis. Since $$w = f \tan \phi_a \, \Omega f n_1 \phi = f \frac{2\, n(u,v)}{\sin|2\alpha|} \quad (12)$$

the co-ordinate $\Delta v'$ is directly proportional to local refractive index difference $\Delta n(u,v,)$, and the shadow pattern therefore shows the refractive index profile. A typical shadow pattern is shown in FIG. 7; the shaded area is the shadow cast onto a screen in the plane u',v', and its correspondence to the preform structure 20 is indicated—the preform has a core 20A and a cladding layer 20B of markedly different refractive index. The slight radial variations in the index of the cladding can be seen. It is an advantage of the FIG. 6 arrangement that very large preforms can be examined because selected small areas of the endface can be displayed and analysed individually.

FIG. 8 illustrates the use of the transmission grating 52 having alternate opaque and transparent areas parallel to the u' axis i.e. orthogonal to the w axis. The grating pitch is d and the grating is positioned at a distance $\delta$ beyond the focal plane of the lens 32. In the image plane u',v', a fringe pattern resembling an interference fringe pattern will be seen, as illustrated in FIG. 9. The relationship between the variable is:

$$v' = \frac{w'q}{\delta} + w\left(1 - \frac{q}{\delta}\right) \quad (13)$$

where w' is the co-ordinate in the plane of the grating 52 parallel to the w direction. The first term of Equation (13) determines the spacing $(dq/\delta)$ of the dark lines in the plane u',v', and the second term indicates the fringe shift s. The fringe shift s is dependent on distance $\delta$, and can be indicated as $\delta'(u,v)$. Then the index difference $\Delta n(u,v)$ on the endface 22 is given by:

$$\Delta n(u,v) = -\frac{1}{2} \frac{\delta'(u,v) \sin|2\alpha|}{f\left(1 - \frac{q}{\delta}\right)} \quad (14)$$

Equation (14) does not include the grating pitch d, but the pitch gives the fringe spacing so it determines the resolution.

For the special case $\delta = o$, i.e. with grating 52 in the focal plane of the lens 32, the fringe pattern in the image plane u',v' takes the form of contour lines of constant refractive index, as illustrated in FIG. 10. The contours are spaced at intervals corresponding to an index increment of $n_\epsilon$, where:

$$n_\epsilon = \frac{d}{2f} \sin|2\alpha| \quad (15)$$

The fringe spacing in the image is proportional to the gradient of the index profile. An attractive modification of this technique is to replace the grating 52 by a multicolour filter having bands of different colours running orthogonal to the w direction. In this case, with white light illumination, the contour lines illustrated in FIGS. 9 and 10 become coloured which allows the differences in index to be more clearly seen.

The apparatus arrangements of FIGS. 4, 5, 6 and 8 give outputs which, while directly related to refractive index profile without the need to apply a mathematical transformation, still need considerable interpretive effort, either by mathematical calculation or by reading by an experienced human eye. It is also possible to give a more easily interpreted two-dimensional visual display of the index distribution in the preform endface. One such arrangement is illustrated in FIG. 11 in which a cylindrical lens 54 is placed in the focal plane of the lens 32, the axis of lens 54 being parallel to the u and u' axes. The cylindrical lens 54 further refracts the rays arriving in the focal plane by an amount which is proportional to their distance w from the optical axis, i.e. in proportion to their refraction angle $\phi$ at the endface 22. If $\beta$ is the secondary refraction angle, then:

$$\tan\beta = \frac{-w}{f' - \tan\phi_a(f' \tan\phi_a - w)} \quad (16)$$

where f' is the focal length of the cylinderical lens 54. If $f' >> \tan \phi_a$ (f' tan $\phi_a$), then:

$$\tan\beta \, \Omega - \frac{w}{f'} \quad (17)$$

The secondary refraction displaces a ray by a distance m in the axial direction of the preform 20, where m depends on the local refractive index $n(u,v)$, and:

$$m = q[\tan(\beta + \phi'') - \tan \phi''] \quad (18)$$

where $\phi''$ is the angle of the ray to the optical axis when the cylindrical lens 54 is absent. If $\tan\beta \tan 0 << 1$, then:

$$m = q \tan\beta$$

Substitution of equation (17) into equation (19) gives:

$$m = -q\frac{w}{f} \quad (20)$$

By using equations (2) and (5), equation (20) can be rewritten as:

$$m = -q\frac{f\,2\Delta n(u,v)}{f'\sin|2\alpha|} \quad (21)$$

Thus the ray shift introduced by the cylindrical lens 54 produces a two dimensional display of the refractive index distribution in the preform endface, since it is in proportion to the local index difference n(u,v) at the point in the endface 22 from which the ray emerged. If the core has a higher index than the preform cladding, the image of the endface is bowed inwards with a corresponding shape.

If the cylindrical lens 54 is moved a distance δ beyond the focal plane of the lens 32 as indicated by the broken line, the ray shift m is then given by:

$$m = \frac{v'p}{qf} - \frac{f\tan\phi_a(q-\delta)^2}{qf'} = \frac{v'p}{qf} - \frac{2\,n(u,v)f(q-\delta)^2}{qf'\sin|2\alpha|} \quad (22)$$

$$\text{where } p = \delta^2 - \delta q + qf' \quad (23)$$

and v' is the ray arrival point in the image plane u',v' when the cylindrical lens 54 is absent. The index profile image then depends on the value of the parameter p; for p>o, the profile of n>n₁ appears inside the preform, as shown in FIG. 12(a) for a typical graded-index preform; for p=o the image becomes a line with only the index profile visible, as shown in FIG. 12(b); and for p<o, the profile of n>n₁ appears to protrude from the preform as in FIG. 12(c).

Figure 13:
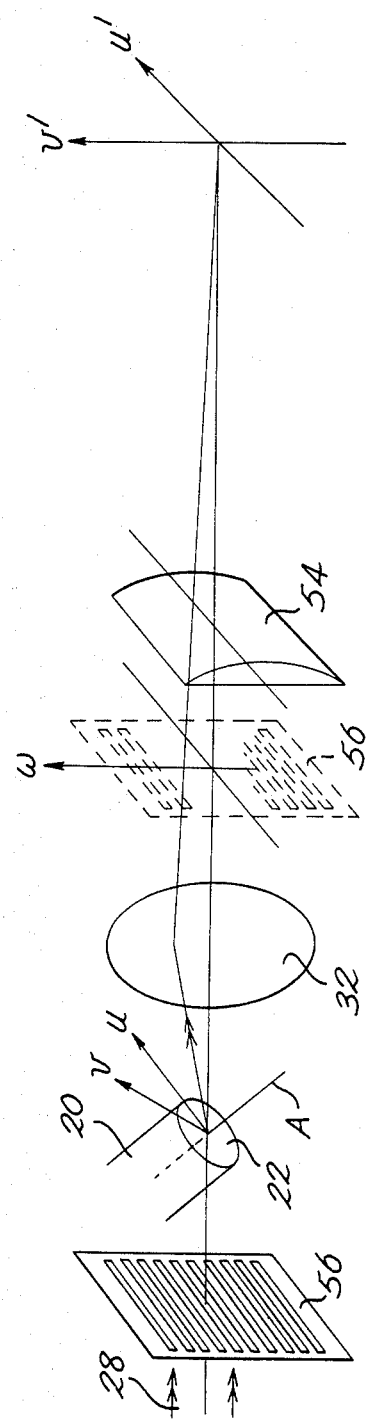
FIG. 13 illustrates use of a cylindrical lens plus a grating, and FIGS. 14($a$), ($b$) and ($c$) show three possible images.
Figure 14C:
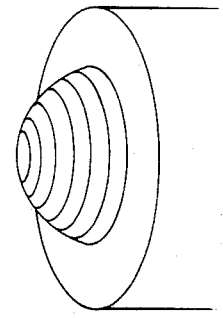
Figure 14B:
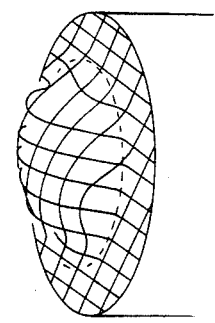
Figure 14A:
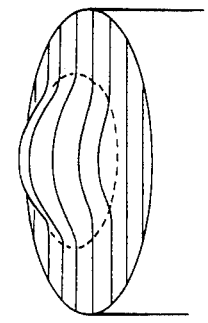

It is often convenient to display the type of image given by the FIG. 11 arrangement with superimposed contour lines. A suitable arrangement is shown in FIG. 13 which is a multipurpose diagram indicating two possible arrangements. In addition to the components shown in FIG. 11, with the cylindrical lens displaced from the image plane, a grating plate 56 can be placed between the illuminating beam 28 and the preform 20. The shadows of the grating lines will appear in the image plane u',v', with distortions due to the ray shafts m given by equation (19). The shadows assist in viewing the profile, as can be seen from FIG. 14(a). If the parallel line grating 56 is replaced by a mesh (not illustrated) which is angled with respect to the axis A of the preform 20, the result would be as shown in FIG. 14(b). If the parallel line grating plate 56 is put in an alternative position, shown dotted, between the lens 32 and the cylindrical lens 54, the image is as shown in FIG. 14(c). The arrangement of FIG. 13 is especially useful for observing the very small index differences typically found in the core of a single-mode optical fibre preform. The use of a colour banded plate instead of grating 56 gives essentially the same displays, but with coloured regions replacing the dark lines.

The modulation systems described with reference to FIGS. 4 to 14 have all relied on spatial modulation of the lens-transformed light. It is also possible to apply a temporal modulation and suitable apparatus is illustrated schematically in FIG. 15. In the focal plane of the spherical lens 32 is a constant-speed rotary light chopper consisting of two blades having straight edges which are radial from the centre of rotation R, i.e. the mark-space ratio as a function of radius is constant. The centre R is offset from the optical axis in a direction parallel to the u' axis. A reference photodiode 60 at a known angular position $\theta_o$ around the blade periphery is connected to a time interval counter 62, and a detecting photodiode 64 is stepped along the u' axis by a control unit 66.

As the light chopper blades rotate at an angular speed p, the edge of each blade sweeps the focal plane in the w direction; for each value of w, the blade first allows illuminating the detector photodiode 64, then as the next blade edge passes, the illumination is cut off, so that the diode output is a series of square pulses. The amount in time at which a light ray is cut on or off depends on its distance in the w direction, and hence on its refraction angle φ from the endface of the preform 20. The reference diode 60 gives a reference or START signal to the counter from its known position $w_o'$, and the diode 64 gives a STOP signal. The variations in time between these two signals detected by the counter 62 as the detector 64 is scanned along the u' axis gives a measure of the angle φ, and hence the local refractive index. The counter output is fed to a computation unit 68 such as a computer and the scan control unit 66 supplies a position signal. The unit 68 applies the calculation given by equation (4), then provides a signal of appropriate form indicating the refractive index function. Note that since the deflection angle φ gives the index n(u,v) at any point u,v in the endface the photodetector can be scanned in any direction, or, for example, in a circle. Note also that either the preform or the photodiode can be moved.

Since the blades 58 describe an arc, and since angle φ to be measured may be large, a tangent correction may be necessary by using:

$$\phi = (R/f)\tan(pt - \theta_o)$$

Figure 16:
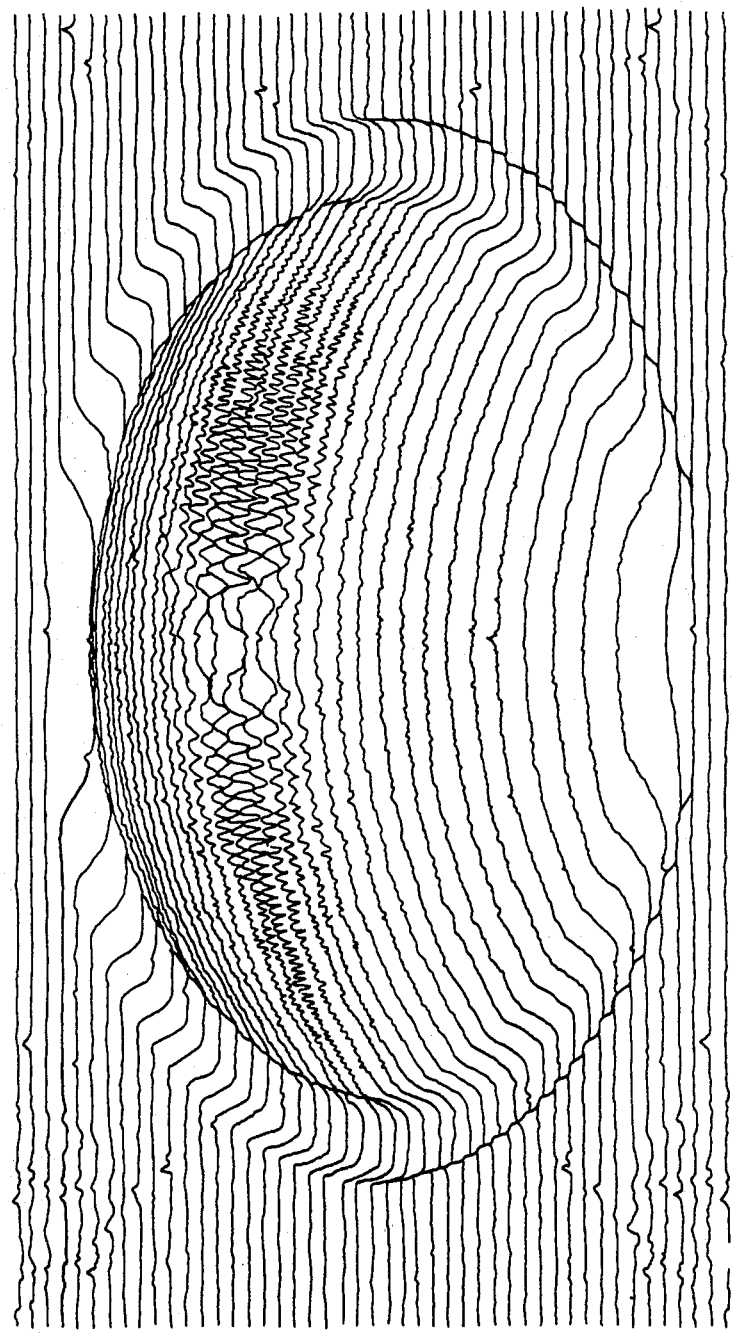
FIG. 16 shows a possible measured refractive index profile in the form of a two-dimensional graphic plot.

Usually the preform 20 in its bath of index-matching fluid will be supported on a scanning table driven by a stepper motor in the direction indicated by the arrows 70 i.e. the v direction. At each position of the preform, the detector 64 is scanned along the u' axis so that a series of signals is provided. A typical output is illustrated in FIG. 16 for a graded-index preform.

Figure 15:
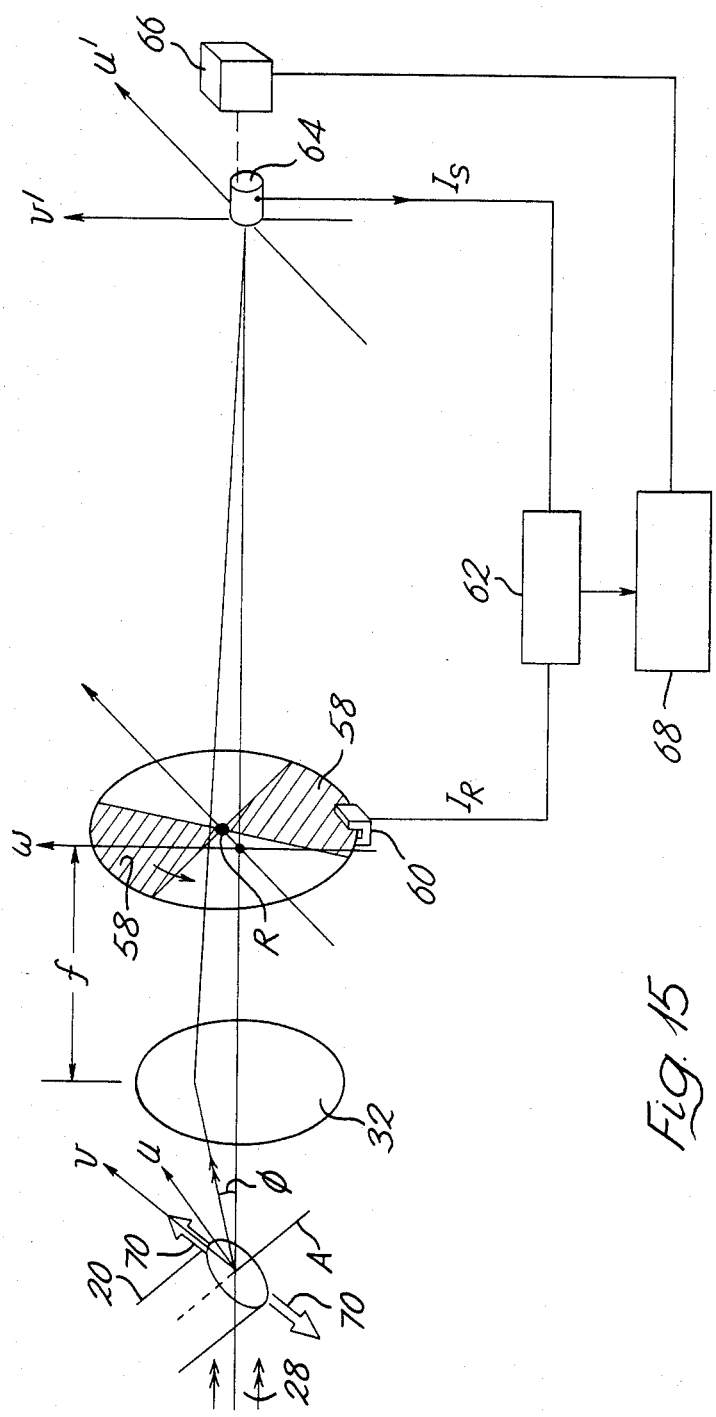
FIG. 15 illustrates temporal modulation.

The FIG. 15 arrangement is the peferred form of apparatus used, because the output is most easily linked to computing means.

It is an advantage of any of the methods of determining refractive index profile described above that the profile is obtainable without a mathematical transformation, so that a profile is obtainable very rapidly. The optical arrangements are all simple, alignment is not critical, and the possibility of direct displays of profile, such as in FIGS. 7, 9, 12 and 14 allows a rapid check of preform quality.

Some arrangements, such as FIGS. 4 to 15, allow high resolution—this is mainly determined by the size of the detector and the image magnification. As previously stated, large preforms and non-circular preforms can be measured.

While end-preparation is required, it can be rapid and no high accuracy is needed; the use of index-matching fluid allows direct use of diamond-sawn ends, although polishing may give slighly less noisy images.

The method depends on the assumption that the refractive index profile is substantially invariant along the axial section which is illuminated during test; usually a length equal to the preform diameter is illuminated.

The invention has been described with reference to a preform having a flat endface perpendicular to its axis A and with the incident beam coplanar with the axis A. If the incident beam and the axis are not coplanar, the angle $\phi$ is measured as the angle of deviation of the ray when projected into the plane containing the preform axis A and optic in the axis Z.

We claim:

1. A method of measuring radial variations in the refractive index of an approximately cylindrical, translucent object having a substantially plane end face and a substantially invariant refractive index in a direction parallel to its axis, comprising illuminating the end face by means of a collimated beam of light incident at an angle to the cylindrical axis which differs substantially from 90 degrees and measuring at a plurality of radial positions the refractive angle at which light leaves the end face.

2. A method of measuring radial variations in refractive index as claimed in claim 1 comprising illuminating the endface with a broad light beam, focussing light emergent from the endface so that the distance from the axis of the focused beam is approximately proportional to the distance from the optical axis in direction coplanar with the endface of the object and optically modulating the focused light in dependence on said distance from the optical axis.

3. A method of measuring radial variations in refractive index as claimed in claim 2 wherein the focused light is optically modulated temporily.

4. A method of measuring radial variations in refractive index as claimed in claim 2 wherein the focused light is modulated spatially.

5. Apparatus for measuring radial variations in the refractive index of an approximately cylindrical, translucent object having substantially plane endface and substantially invariant refracrive index in a direction parallel to its axis comprising an illumination source positioned to direct a collimated beam of light on the said endface at an angle to the axis of said object which differs substantially from 90 degrees, focussing means positioned to receive and focus said beam of light on emergence from said end face and sensing means to determine the angle of emergence of said light beam from said endface as a function of the position of emergence of said light beam.

6. Apparatus for measuring radial variations of refractive index as claimed in claim 5 having modulating means positioned in the path of said light beam between said focussing means and said sensing means.

7. Apparatus as claimed in claim 6 wherein said modulating means is adapted to modulate the intensity of said light beam as a function of the distance of said light beam from the optical axis of said focussing and measuring system.

8. Apparatus as claimed in claim 7 wherein said modulating means comprises a filter having a graded attenuation.

9. Apparatus as claimed in claim 7 wherein said modulating means comprises a shutter movable in a direction normal to said optical axis.

10. Apparatus as claimed in claim 7 wherein said modulating means comprises a grating having alternate opaque and transparent regions orthogonal to said axis.

11. Apparatus as claimed in claim 7 wherein said modulating means comprises a cylindrical lens.

12. Apparatus as claimed in claim 6 wherein said modulating means is adapted to modulate temporily the intensity of said light beam.

13. Apparatus as claimed in claim 11 wherein said modulating means comprises a shutter means rotatable about an axis parallel to the optical axis of said focussing and measuring means and positioned apart therefrom.

* * * * *